United States Patent [19]

Callahan et al.

[11] 4,444,906

[45] Apr. 24, 1984

[54] METHOD FOR THE PREPARATION OF HIGH ACTIVITY PHOSPHOMOLYBDIC ACID BASED CATALYSTS

[75] Inventors: James L. Callahan, Wooster; Wilfrid G. Shaw; Arthur F. Miller, both of Lyndhurst, all of Ohio

[73] Assignee: The Standard Oil Company, Cleveland, Ohio

[21] Appl. No.: 439,952

[22] Filed: Nov. 8, 1982

Related U.S. Application Data

[62] Division of Ser. No. 271,458, Jun. 8, 1981, abandoned.

[51] Int. Cl.$^3$ ............................................... B01J 27/14
[52] U.S. Cl. .................................... 502/211; 502/209; 502/210; 502/212
[58] Field of Search ................................ 252/435, 437

[56] References Cited

U.S. PATENT DOCUMENTS

| | | | |
|---|---|---|---|
| 3,642,930 | 2/1972 | Grasselli et al. | 252/437 X |
| 3,865,873 | 2/1975 | Oda et al. | 252/437 X |
| 3,882,047 | 5/1975 | Niina et al. | 252/437 X |
| 3,956,181 | 5/1976 | Grasselli et al. | 252/437 X |
| 3,975,300 | 8/1976 | Burress | 252/437 X |
| 4,000,088 | 12/1976 | Shimizu et al. | 252/437 |
| 4,001,316 | 1/1977 | Ishiwi | 252/437 |
| 4,003,978 | 1/1977 | Shiraishi et al. | 252/437 X |
| 4,035,417 | 7/1977 | Izawa et al. | 252/437 X |
| 4,077,912 | 3/1978 | Dolhyj et al. | 252/461 |
| 4,083,805 | 4/1978 | White et al. | 252/437 |
| 4,138,366 | 2/1979 | Shaw et al. | 252/437 X |
| 4,147,661 | 4/1979 | Higgins et al. | 252/437 X |
| 4,192,951 | 3/1980 | Slinkard et al. | 252/437 X |
| 4,251,393 | 2/1981 | Dalton et al. | 252/456 X |
| 4,276,222 | 6/1981 | Mount et al. | 252/437 X |
| 4,312,787 | 1/1982 | Dolhyj et al. | 252/435 |

*Primary Examiner*—Delbert E. Gantz
*Assistant Examiner*—William G. Wright
*Attorney, Agent, or Firm*—Joseph G. Curatolo; Larry W. Evans

[57] ABSTRACT

The present invention relates to a method for the preparation of phosphomolybdic acid based catalysts by forming a solution of hydrated phosphomolybdic acid in a substantially anhydrous alkyl alcohol, adding a base to the solution, evaporating the solution to yield a catalyst powder and thereafter drying and calcining the powder to form the active catalysts. A second method for preparation is also provided and includes the steps of forming a solution of hydrated phosphomolybdic acid in a substantially anhydrous alkyl alcohol, evaporating the solution to form a concentrate, impregnating a catalyst support material with the concentrate, contacting the impregnated support with ammonia gas in an amount sufficient to form an insoluble precipitate of ammonium alkyl phosphomolybdic acid within the pore structure of said support material and thereafter drying and calcining said impregnated support material so as to form a coated catalyst.

20 Claims, No Drawings

METHOD FOR THE PREPARATION OF HIGH ACTIVITY PHOSPHOMOLYBDIC ACID BASED CATALYSTS

This is a division of application Ser. No. 271,458 filed June 8, 1981, now abandoned.

TECHNICAL FIELD

Catalysts comprising phosphomolybdic acid and various salts thereof have recognized utility in several areas of petrochemical processing. An area of particular importance which relates to the present invention is the use of phosphomolybdic acid based compounds as catalysts for the selective direct oxidation of aldehydes such as isobutyraldehyd and methacrolein to their corresponding carboxylic acid, methacrylic acid. Catalysis with supported or unsupported dehydrated phosphomolybdic acid in combination with small amounts of promoters such as antimony, arsenic, bismuth, copper, tellurium and hydroxides and decomposable salts of alkali and alkaline earth metals is a process of specific economic interest. The subject invention sets forth a method for the preparation of phosphomolybdic acid based catalysts having a high activity for the more efficient conversion of aldehydes to unsaturated carboxylic acids.

BACKGROUND ART

Catalysts for the oxidation of unsaturated aldehydes to unsaturated acids are generally well known in the literature and in various patents. U.S. Pat. Nos. 3,865,873 and 3,882,047 and Japanese Pat. No. 47-33082 disclose such catalysts wherein ammonia or an ammonium-containing compound is incorporated in the preparation of the catalysts.

U.S. Pat. No. 2,865,873 in Column 13, Examples 101 to 104 discloses a process for the preparation of methacrylic acid using catalysts consisting of molybdenum, phosphorus, titanium and oxygen, wherein ammonium para-molybdate is employed in the preparation of the catalysts. The highest yield of methacrylic acid produced is about 39.56%.

U.S. Pat. No. 3,882,047 discloses the preparation of methacrylic acid using catalysts containing molybdenum, phosphorus, at least one element such as thallium, rubidium, cesium and potassium, and at least one element such as chromium, silicon, aluminum, iron and titanium. This reference teaches the incorporation of ammonia or ammonium-containing compounds in the preparation of catalysts exemplified in the oxidation of methacrolein or acrolein; phosphomolybdic acid is employed in the preparation of virtually all catalysts exemplified; and in a few examples, ammonium molybdate is employed. This patent discloses in column 3, lines 30–40 as follows:

"It is preferred that the catalyst be prepared so that the constituent elements will form complex compounds such as heteropolyacids, then acid salts or ammonium salts."

Japanese Pat. No. 47-33082 discloses a process for reclaiming an ammonia-modified phosphorous-molybdenum-X-oxygen catalyst, wherein X is at least one element selected from the group consisting of antimony, arsenic, bismuth, cadmium, germanium, indium, iron, lead, silicon, thallium, tin and tungsten. Preparation of the catalyst involves treating the catalyst with the ammonia and water by oxidizing the catalyst in advance or by oxidizing it simultaneously with the treatment of ammonia and water. This patent discloses that the ammonia forms a complex compound with the other elements present.

Preparation of phosphomolybdic acid based catalyst in the absence of ammonia or ammonia-containing compound is described in U.S. Pat. No. 4,136,110, commonly owned by the Assignee of record herein. However, the process set forth therein is also directed toward catalyst preparation from molybdenum trioxide. Thus, the prior art of which we are aware has not set forth a method by which a phosphomolybdic acid based catalyst can be prepared in aqueous media from phosphomolybdic acid in the absence of ammonia or other basic compound.

Copending application Ser. No. 222,821 by Grasselli et al., assigned by our common Assignee herein, is directed to the preparation of first stage oxide catalysts containing molybdenum and one of bismuth or tellurium in an organic liquid preferably admixed with 5 to 35% water.

U.S. Pat. Nos. 3,959,182 and 4,035,417 disclose the preparation of molybdenum vanadate catalysts having a molybdenum oxide to vanadium oxide weight ratio of 2:1 to 8:1 in an aqueous solution to which is added various organic reducing agents. The liquid media exemplified contain between 4 to 8% organics by weight.

U.S. Pat. No. 4,000,088 discloses the aqueous preparation of phosphomolybdic acid based catalysts utilizing a solution of catalyst components, that upon mixing with aqueous 28% ammonia water, results in a suspension.

Thus it can be seen that the prior art is characterized by the utilization of ammonia or an ammonia-containing compound for the preparation of phosphomolybdic acid based catalysts. It is believed that treatment with ammonia has been employed to react with groups in the catalyst which would otherwise undergo crosslinking during drying and early calcination, a process which significantly deactivates the catalyst before it is even used. Preparation of phosphomolybdic acid based catalysts in alcohol is believed to provide protection for more of these groups than when an aqueous ammoniation process is employed thereby providing a higher activity of the phosphomolybdic acid based catalyst.

DISCLOSURE OF THE INVENTION

It is therefore an object of the present invention to provide methods for the preparation of phosphomolybic acid based catalysts utilized in the oxidation of aldehydes to unsaturated carboxylic acids.

It is another object of the present invention to provide methods for the preparation of phosphomolybdic acid based catalysts utilizing phosphomolybdic acid in the presence of alcohol followed by the addition of ammonia or an amine base to provide a resulting catalyst of high activity.

It is yet another object of the present invention to provide methods for the preparation of phosphomolybdic acid based catalysts in an alcoholic catalyst solution thereby avoiding gross precipitation of solids.

It is still another object of the present invention to provide methods for the preparation of phosphomolybdic acid based catalysts in an alcoholic catalyst solution which permits the impregnation of porous preformed supports.

These and other objects, together with the advantages thereof over known methods, which shall become apparent from the specification which follows, are accomplished by the invention as hereinafter described and claimed.

In general, one method of the present invention involves the steps of forming a solution of hydrated phosphomolybdic acid in a substantially anhydrous alcohol, adding a base to the solution, heating the solution to form a powder, and thereafter calcining the powder to form the active catalyst. If desired, suitable promoter-containing compounds may be added during the steps of forming a solution.

A second method is also provided wherein the step of adding the base to the alcoholic catalyst solution is deleted. A catalyst component solution is obtained and used to impregnate a catalyst support material. Treatment with a volatile base follows which includes the step of contacting the impregnated catalyst support material with ammonia gas, and thereafter drying and calcining the impregnated support.

PREFERRED MODE FOR CARRYING OUT THE INVENTION

The inventive catalyst preparation technique is applicable to phosphomolybdic acid based catalysts which are known in the art as second stage catalysts. This is in contrast to the method disclosed in U.S. Ser. No. 222,281 to Grasselli et al., assigned to our common Assignee and directed to the preparation of bismuth molybdate first stage catalysts in a precatalyst slurry in an organic liquid or a mixture of an organic liquid and water. By "first stage" catalysts is meant that the catalysts show good activity in the conversion of olefins to aldehydes such as propylene to acrolein but poor activity in the conversion of aldehydes to acids such as acrolein to acrylic acid. First stage catalysts are distinguished from "second stage" catalysts, which are catalysts showing poor activity in the conversion of propylene to acrolein but good activity in the conversion of acrolein to acrylic acid, and still other oxidation catalysts which are neither first stage catalysts nor second stage catalysts, e.g. maleic anhydride catalysts.

Because of the complexity of oxide complex oxidation catalysts, there is no clear understanding in the art of exactly what features of a catalyst (e.g. composition, crystal structure, calcination history, etc.) make it function as a first stage, second stage or different type of catalyst. Certain observations, however, can be made. For example, second stage catalysts cannot normally be calcined for any length of time at temperatures above about 1,000° F. (537° C.), since they lose most if not all of their activity is treated in this way. On the other hand, first stage catalysts work best is calcined (final calcination) above 1,000° F., such as for example at 610° C. In addition, it appears that first stage catalysts are "neutral" in character while second stage catalysts are "acidic" in character.

Empirically it is possible to make a rough approximation of the acidic or basic character of an oxide complex by comparing the total positive valences of the cationic elements with the total negative valences of the metalate moieties derived from the anionic acting elements. Because some cationic elements such as iron may exist in more than one valence state and because of the amphoteric elements, this approximation cannot be too exact. In any event, using this type analysis it appears that most second stage catalysts have a significant excess of anionic species, i.e. are highly acidic, while most first stage catalysts have a reasonable balance of cationic and anionic ingredients and hence are relatively neutral. Analytically, however, it is extremely difficult or impossible to determine if such oxide complexes, which are oxides and not acids or bases, exhibit an acidic or basic character. For this reason, the "neutral"/"acid" designations for first and second stage catalysts are still regarded as unconfirmed speculation. However, it is known that first and second stage catalysts are materially different from one another and from catalysts exhibiting neither first stage activity or second stage activity and that these differences can easily be determined by testing the catalyst in the first and second stage reactions as described above.

The catalyst commonly employed in the preparation of methacrylic acid from methacrolein or isobutyraldehyde and acrylic acid from acrolein is a phosphomolybdic acid based catalyst which can be provided with one or more metallic promoters and which has the general formula $Mo_xP_yA_aB_bC_cD_dE_eO_z$. Suitable promoters include the following: wherein A is ammonium, cesium, potassium, rubidium and/or thallium; B is copper and/or vanadium; C is antimomy, arsenic, bismuth and/or tellurium; D is palladium; E is aluminum, barium, calcium, cerium, chromium, cobalt, iron, magnesium, manganese, nickel, tantalum, titanium, tungsten, zinc, zirconium, chlorine and/or bromine; and, wherein x can be 6 to 14 and is preferably 9 to 12, y can be 0.1 to 15 and is preferably 1 to 1.5, a can be 0.1 to 3 and is preferably 1 to 2, b can be 0.1 to 3 and is preferably 0.1 to 1, c can be 0 to 2 and is preferably 0 to 0.7, d can be 0 to 2 and is preferably 0 to 1, e can be 0 to 4 and is preferably 0 to 1, and z is a number necessary to satisfy the other elements. Suitable catalysts and the preparation thereof have been described in several U.S. patents commonly owned by the Assignee of record herein and include, for instance, U.S. Pat. Nos. 4,083,805 and 4,138,366. Of these many catalysts, those having a ratio of molybdenum to phosphorus or from about 3:1 to as high as 15:1 can be employed with 9 to 12:1 being preferred. Addition of these promoters can be made by employing the acids or decomposable salts of the promoters.

Inasmuch as these catalysts are known, the specific composition is not critical to the practice of the method set forth therein. Thus, while a particular formulation is employed in this disclosure by way of exemplification, it is to be understood that phosphomolybdic acid based compositions having other promoters could also be prepared according to the present invention.

Actual preparation of the catalyst involves as a first step the dissolving of hydrated phosphomolybdic acid in a substantially anhydrous alkyl alcohol. The preferred alcohol employed is ethanol although other lower alkyl alcohols having one to about five carbon atoms can be substituted therefor. Representative alcohols include but are not limited to methanol, ethanol, isopropanol, isobutanol and the like. The catalyst promoters can be added in some instances as acids or as salts. The one or more that is selected is also preferably dissolved in the substantially anhydrous alcohol so that the alcohol solution comprises a mixture of hydrated phosphomolybdic acid and the promoter-containing compounds.

It is necessary that the alcohol is substantially anhydrous. The presence of significant amounts of water in the solution diminishes the enhancement of catalyst processing and activity achieved by utilization of the alcohol solution.

Next, the solution can be heated after which a base is added such as ammonium hydroxide to form insoluble salts having the formula $(NH_4)_xR_yPMA$, where R is the residue from the alcohol and x and y are belived to be the integers 1 or 2 with the proviso that they not be the same. Suitable bases also include tetraalkyl ammonium hyroxides, wherein the alkyl group contains four to about 16 carbon atoms, and various amines such as trimethylamine.

The first heating is conducted at a temperature about 78° C., the boiling point of alcohol, i.e., for ethanol, for approximately 15 minutes. Addition of the base should bring the pH to about 2 to 6. The solution is thereafter evaporated and heated at about 150° C., leaving a powder or residue which is, in turn, calcined above 300° C. for about 2 hours to yield the active catalyst. The catalyst may be tabletted or pelleted. If desired, the solidified residue can be dispersed in alcohol and used to coat a catalyst support. Alternatively, the catalyst support can be wetted with the alcohol and coated with the catalyst powder. (e.g. by the method set forth in U.S. Pat. No. 4,077,912.) Suitable support materials include silica, alumina, silica-alumina boron-phosphate, silicon-carbide, niobium oxide, titania, zirconia and the like and preferably Alundum as well as mixtures thereof; the amount of active ingredient in the finished catalyst being from about 10 to 100 percent by weight and preferably up to about 70 percent. The coated catalyst is then given the step of calcining.

In the example which follows, a phosphomolybdic acid based catalyst having the composition $Mo_{10}PAs_{0.2}Cu_{0.2}O_z$ was prepared and coated on Alundum having a particle size between 10 and 20 mesh. Weight percent of active catalyst was 28.6. The catalyst thus prepared was thereafter tested for methacrolein oxidation at 375° C. In order to evaluate the effectiveness of the method set forth herein, a measurement of percent per single pass yield or percent yield was made, which is defined as follows:

Percent Single Pass Yield = (Moles of product recovered)/(Moles of reactant fed) × 100

EXAMPLE 1.2510 gm of $20 MoO_3.2H_3PO_4.48H_2O$ was dissolved in 10 cc of substantially anhydrous ethanol with heating and stirring. Two additional solutions were made by dissolving 0.0202 gm of $H_3AsO_4.0.5H_2O$ and 0.0254 gm of $Cu(C_2H_3O_2)_2.H_2O$ in 3 cc of substantially anhydrous ethanol each. Both of these solutions were then added to the phosphomolybdic acid solution and the resulting mixture was heated with stirring at moderate heat for 15 minutes. Then the pH was adjusted to 5 by adding 29.8% ammonium hydroxide drop-wise. The resulting mixture was evaporated and dried for 30 minutes at 150° C. to yield a powder. The powder was used to coat 10 to 20 mesh Alundum particles at the 28.5 weight percent level which particles were thereafter dried for two hours at 150° C. and calcined for two hours at 320° C.

The resulting second stage catalyst was thereafter utilized with a conventional first stage catalyst to oxidize isobutylene to methacrolein and then methacrylic acid as follows: 2 cc of the second stage phosphomolybdic acid based catalyst was placed over 4 cc of the first stage oxidation catalyst. Testing was conducted in a flow microreactor consisting of a 0.79 cm I.D. × 16.51 cm long stainless steel tube immersed in a molten salt bath at 375° C. and atmospheric pressure. Reactant feed comprising air, water and isobutylene, molar ratio of 12:3:1, was introduced into the bottom of the reactor through a 0.48 cm O.D. stainless steel preheat leg; the reactor and preheat leg forming a U-tube configuration. Within the reactor was a suitable first stage catalyst for the conversion of isobutylene to methacrolein on top of which was stacked the candidate second stage catalyst for the conversion of methacrolein to methacrylic acid. Process water was fed through a silicone rubber septum at the top of the preheat leg with a model 355 Sage syringe pump being used to regulate the process water flow rate. First stage conversion, i.e., isobutylene to methacrolein, was conducted by feeding isobutylene, air and water through the microreactor for an apparent contact time with 4 cc of the first stage catalyst of two seconds. The particular first stage catalyst employed was 20% silica and 80% active ingredients, the latter comprising a nickel-cobalt promoted bismuth molybdate catalyst as disclosed in U.S. Pat. No. 3,642,930. Results of the first stage oxidation were 98% total conversion with 76% yield of methacrolein, 11% methacrylic acid and the remainder being oxides of carbon. For the second stage conversion, methacrolein to methacrylic acid, an apparent contact time of one second was provided. The second stage catalyst was at the 28.6 weight percent level, supported on 10-20 mesh Alundum particles. Percent yields after the second stage oxidation were as follows:

Methacrolein: 24.4
Methacrylic Acid: 54.0

From the analysis of the products it was determined that isobutylene conversion was 100 percent. The formula for isobutylene conversion is as follows:

(Moles of isobutylene reacted)/(Moles of isobutylene fed) × 100

According to the second method provided herein, the solution of phosphomolybdic acid and other catalyst components is prepared as disclosed in the foregoing example. Without the addition of ammonium hydroxide, the alcoholic solution is boiled down to a volume sufficient to fill the pores and wet-out the surface of preformed fluid Alundum particles such that the finished catalyst will have a concentration of about 25 percent by weight ingredient. At this point, the catalyst is contacted with ammonia gas in an amount sufficient to cause the insoluble precipitate $NH_4(C_2H_5)_2PMA$ to be formed with the pore structure of the support material.

Such contacting with ammonia gas may be accomplished by diluting the ammonia with air or nitrogen and conducting the gas-solid exposure in a fluidized-bed, if desired. After the in-particle precipitation is accomplished, the temperature of the catalyst bed is raised from an initial temperature of about 80° C. to about 320° C. over the course of 2 hours. The catalyst is maintained at the 320° C. calcination temperature for an additional 2 hours and after this treatment is ready for process service. It will be understood that other calcining temperatures, i.e., 300° C. to about 450° C., could be used for alternate catalyst compositions.

Thus, it can be seen that the methods set forth herein are effective in the preparation of phosphomolybdic acid based catalysts. Unlike conventional activation methods, which employ aqueous solutions of phosphomolybdic acid with or without promoters, the use of an alcoholic solution does not depend solely upon treatment with ammonia or similar basic compounds to provide the catalyst material. The utility of the lower alcohols in this regard depends on their solvency for phosphomolybdic acid and other catalyst constituents and on their ability to undergo chemical reaction with and solubilize the phosphomolybdic acid.

Another important aspect of this method of catalyst preparation is in fact that by utilizing an alcoholic catalyst solution, the properties of a true solution are maintained, that is, there is no gross precipitation of solids, even in highly concentrated solution, however, the precipitate can eventually be formed by the use of ammonia. By contrast, in the conventional preparations from aqueous solution, ammonium ion must be introduced leading to gross precipitation of insoluble ammonium phosphompolybdate.

Another important consequence of the solution property of the phosphomolybdic acid alcohol system is that it permits the impregnation of porous preformed supports. This opportunity is not present where a large amount of the catalyst components exist as suspended solids within the impregnating fluid. The ability to impregnate a preformed porous support to produce an active and attrition resistant catalyst particle is particularly important in fluid-bed catalytic processing applications.

A further advantage of the phosphomolybdic acid-alcohol-ammonia system resides in the better protection of particular chemical groupings in the final drying and early calcination stages of catalyst preparation, afforded first by use of alcohol rather than ammonium ion, subsequently followed by treatment to incorporate the ammonium ion. This superiority of the alcohol in combination with ammonia is reflected in the high level of activity of the finished phosphomolybdic acid based catalyst.

The present invention provides a process for the production of unsaturated carboxylic acids from their corresponding aldehydes, saturated or unsaturated, in the presence of a phosphomolybdic acid based catalyst prepared as described above. The aldehyde is contacted with molecular oxygen in the vapor phase at a reaction temperature of about 200° C. to about 500° C. in the presence of the catalyst. Reaction pressure may be subatmospheric, atmospheric, or superatmospheric. The reaction may be conducted in fixed or fluid bed reactors.

Based upon the satisfactory yields of methacrylic acid that have been obtained when phosphomolybdic acid based catalysts are prepared according to the methods set forth herein, it should be apparent that the objects of the invention have been met. It is to be understood that the preparation disclosed herein is applicable in general to phosphomolybdic acid based catalysts which, as stated hereinabove, can include one or more promoters or promoter-containing compounds. Presence of absence of these additional elements or compounds will not affect the method of preparation set forth herein.

It should also be apparent to those skilled in the art that the subject invention is operable on phosphomolybdic acid based catalysts having certain ratios of molybdenum to phosphorus and it is operable when certain alcohols, bases, temperatures and catalyst supports are employed. It is to be understood that these variables fall within the scope of the claimed invention and that the subject invention is not to be limited by the example are forth herein. It has been provided merely to provide a demonstration of operability and it is believed that the selection of specific alcohols and reaction conditions can be determined without departing from the spirit of the invention herein disclosed and described, and that the scope of the invention shall include all modifications and variations that fall within the scope of the attached claims.

We claim:

1. A method for the preparation of a second stage phosphomolybdic acid based catalysts comprising the steps of:
    forming a solution of hydrated phosphomolybdic acid in a substantially anhydrous alkyl alcohol;
    adding a base to said solution;
    evaporating said solution to yield a catalyst powder; and
    drying and calcining said powder to form the active catalyst.

2. A method for the preparation of phosphomolybdic acid based catalysts, as set forth in claim 1, including the additional step of adding at least one promoter-containing compound selected from the group consisting of acids and decomposable salts of promoters selected from the group consisting of ammonium, cesium, potassium, ribidium, thallium, copper, vanadium antimony, arsenic, bismuth, tellurium, palladium, aluminum, barium, calcium, cerium, chromium, cobalt, iron, magnesium, manganese, nickel, tantalum, titanium, tungsten, zinc, zirconium, chlorine and bromine.

3. A method for the preparation of phosphomolybdic acid based catalysts, as set forth in claim 1, wherein said base is selected from the group consisting of ammonium hydroxide, amines and tetraalkyl ammonium hydroxides having from four to about 16 carbon atoms.

4. A method for the preparation of phosphomolybdic acid based catalysts, as set forth in claim 3, wherein said base is ammonium hydroxide.

5. A method for the preparation of phosphomolybdic acid based catalysts, as set forth in claim 1, including the additional steps of
    dispersing said catalyst powder in a substantially anhydrous alkyl alcohol; and
    impregnating a catalyst support material therewith prior to said steps of drying and calcining.

6. A method for the preparation of phosphomolybdic acid based catalysts, as set forth in claim 1, including the additional steps of
    wetting a catalyst support material with a substantially anhydrous alkyl alcohol; and
    mixing said catalyst powder with said wetted support prior to said steps of drying and calcining.

7. A method for the preparation of phosphomolybdic acid based catalysts, as set forth in claim 1 wherein the step of drying is conducted at a temperature of at least 150° C. and the step of calcining is conducted at a temperature of at least 300° C.

8. A method for the preparation of phosphomolybdic acid based catalysts, as set forth in claim 2, wherein said phosphomolybdic acid based catalyst has the formula $Mo_xP_yA_aB_bC_cD_dE_eO_z$ wherein A is selected from the group consisting of ammonium, cesium, potassium, rubidium and thallium; B is selected from the group consisting of copper and vanadium; C is selected from the group consisting of antimony, arsenic, bismuth and tellurium; D is palladium; E is aluminum, barium, calcium, cerium, chromium, cobalt, iron, magnesium, manganese, nickel, tantalum, titanium, tungsten, zinc, zirconium, chlorine and bromine; x is 6 to 14; y is 0.1 to 15; a is 0.1 to 3; b is 0.1 to 3; c is 0 to 2; d is 0 to 2; e is 0 to 4 and z is a number necessary to satisfy the other elements.

9. A method for the preparation of phosphomolybdic acid based catalysts, as set forth in claim 8, wherein x is 9 to 12; y is 1 to 1.5; a is 1 to 2; b is 0.1 to 1; c is 0 to 0.7; d is 0 to 1 and e is 0 to 1.

10. A method for the preparation of phosphomolybdic acid based catalysts, as set forth in claim 9, wherein the composition of said phosphomolybdic acid based catalyst is $Mo_{10}PAs_{0.2}Cu_{0.2}O_z$.

11. A method for the preparation of phosphomolybdic acid based catalysts, as set forth in claim 5 wherein said catalyst support material is selected from the group consisting of alumina, Alundum, boron-phosphate, silica, alumina-silica, silicon carbide, niobium oxide, titania, zirconia and mistures thereof.

12. A method for the preparation of phosphomolybdic acid based catalysts, as set forth in claim 6 wherein said catalyst support material is selected from the group consisting of alumina, Alundum, boron-phosphate, silica, alumina-silica, silicon carbide, niobium oxide, titania, zirzonia and mistures thereof.

13. A method for the preparation of second stage phosphomolybdic acid based catalysts comprising the steps of:
    forming a solution of hydrated phosphomolybdic acid in a substantially anhydrous alkyl alcohol;
    evaporating said solution to form a concentrate;
    treating a catalyst support material with said concentrate;
    contacting said treated support with ammonia gas in an amount sufficient to form an insoluble precipitate of ammonium alkyl phosphomolybdic acid within the pore structure of said support material; and
    drying and calcining said treated support material so as to form the final catalyst.

14. A method for the preparation of phosphomolybdic acid based catalysts, as set forth in claim 13, wherein the step of evaporating is conducted until the volume has been reduced sufficiently for the catalyst mixture to fill the pore volume and wet-out the surface of said catalyst support material.

15. A method for the preparation of phosphomolybdic acid based catalysts, as set forth in claim 13, wherein the step of evaporating is conducted until said concentrate is a powder, and the step of treating a catalyst support includes the steps of
    wetting said catalyst support with a substantially anhydrous alkyl alcohol; and
    mixing said powder with said wetted support.

16. A method for the preparation of phosphomolybdic acid based catalysts, as set forth in claim 13, wherein the step of treating said catalyst support material including the steps of
    dispersing said concentrate in a substantially anhydrous alkyl alcohol;
    impregnating said support material therewith; and
    evaporating said alcohol.

17. A method for the preparation of phosphomolybdic acid based catalysts, as set forth in claim 13 wherein said catalyst support material is selected from the group consisting of alumina, Alundum, boron-phosphate, silica, alumina-silica, silicon carbide, niobium oxide, titania, zirconia and mixtures thereof.

18. A method for the preparation of phosphomolybdic acid based catalysts, as set forth in claim 13 wherein the step of drying is conducted at a temperature of at least 150° C. and the step of calcining is conducted at a temperature of at least 300° C.

19. A method for the preparation of phosphomolybdic acid based catalysts, as set forth in claim 1, 13, 5, 6, 15 or 16, wherein said substantially anhydrous alkyl alcohol has from one to about five carbon atoms.

20. A method for the preparation of phosphomolybdic acid based catalysts, as set forth in claim 19, wherein said substantially anhydrous alkyl alcohol is ethanol.

* * * * *